(12) United States Patent
Pratt et al.

(10) Patent No.: US 8,359,166 B2
(45) Date of Patent: Jan. 22, 2013

(54) METHOD AND SYSTEM FOR GENOTYPING SAMPLES IN A NORMALIZED ALLELIC SPACE

(75) Inventors: Mark R. Pratt, San Mateo, CA (US); David P. Holden, Burlingame, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 299 days.

(21) Appl. No.: 12/551,438

(22) Filed: Aug. 31, 2009

(65) Prior Publication Data

US 2010/0161237 A1    Jun. 24, 2010

Related U.S. Application Data

(63) Continuation of application No. 11/259,162, filed on Oct. 25, 2005, now abandoned.

(60) Provisional application No. 60/622,279, filed on Oct. 25, 2004.

(51) Int. Cl.
  *G06F 19/00*    (2011.01)
  *G06F 15/00*    (2006.01)
  *G11C 17/00*    (2006.01)

(52) U.S. Cl. .................................. 702/20; 365/94; 700/1

(58) Field of Classification Search ........................ None
See application file for complete search history.

(56) References Cited

U.S. PATENT DOCUMENTS 6,274,317 B1 *   8/2001   Hiller et al. .................. 435/6.14
2003/0186279 A1 *  10/2003   Kennedy et al. .................. 435/6

OTHER PUBLICATIONS

Gordon et al. Assessment and management of single nucleotide polymorphism genotype errors in genetic association analysis Pacific Symposium on Biocomputing vol. 6, pp. 18-29 (2001).*

* cited by examiner

*Primary Examiner* — John S Brusca (57) ABSTRACT

Aspects of the present invention describe an apparatus and method for generating genotype calls for a sample. The genotyping initially models allelic signal response into an allelic model having one or more model parameters for an identified one or more sources of systematic variation. The model and parameters are then used to transform the allelic signals to a normalized normalized allelic space that serves to compensate for the one or more sources of systematic variation. By compensating for the systematic variation in this manner, the genotype for the sample is readily determined based upon its relationship to the representation of the allelic signals in normalized allelic space and in accordance with the allelic model.

14 Claims, 8 Drawing Sheets

METHOD AND SYSTEM FOR GENOTYPING SAMPLES IN A NORMALIZED ALLELIC SPACE

CROSS-REFERENCE TO RELATED APPLICATIONS

This application claims priority to U.S. Provisional Application No. 60/622,279, filed Oct. 25, 2004 assigned to the assignee of the present invention and titled "Self Calibration and Joint Modeling of High Throughput Genotype Data", and to U.S. patent application Ser. No. 11/259,162, both of which is incorporated herein by reference.

INTRODUCTION

Genotyping analysis can be hampered by noise and other perturbations affecting signal response. Oftentimes, conventional approaches to determine genotype calls inadequately address resolving these factors thus increasing the uncertainty and subjectivity of the analysis. In certain instances, conventional genotyping routines may discard data that does not conform to an identifiable signal cluster despite the overall effort to keep this information.

Removal of data from a sample set in this manner may actually prevent identification of critical data points and reduce the overall efficiency of the genotyping analysis. Further, including noisy allele signal response may reduce genotype call accuracy as it can skew or throw off certain conventional genotyping approaches.

Improved computational processing of genetic samples and their associated signal responses is of growing importance. This is especially true in the context of high throughput platforms such as SNPlex® by Applied Biosystems Corporation that are capable of performing genotyping on smaller reaction volumes and larger multiplexed assays. For such systems, it is desirable to maintain the ability to operate at high speeds while producing accurate results even with data that is conventionally difficult to evaluate.

BRIEF DESCRIPTION OF THE DRAWINGS

The skilled artisan will understand that the drawings, described below, are for illustration purposes only. The drawings are not intended to limit the scope of the present teachings in any way.

SUMMARY

Aspects of the present invention describe an apparatus and method for generating genotype calls for one or more samples. The genotyping approach transforms and corrects for systematic variation in an allelic signal response with an allelic model represented with one or more model parameters. The parameters in the model are associated with noise and other sources of systematic variation. The model and parameters may then be used to transform the allelic signals into a representation of normalized allelic space that serves to compensate for the one or more sources of the noise or systematic variation. In various implementations, systematic variation may arise from instrument artifacts, chemistry artifacts, process artifacts, operational artifacts, temperature artifacts, humidity artifacts, volume artifacts and assay artifacts. Compensating for these variations in this manner, makes it possible to determine the genotype for the sample based upon its relationship to the representation of the allelic signals in normalized allelic space and in accordance with the allelic model.

These and other features of the present teachings are set forth herein.

DESCRIPTION

Figure 1:
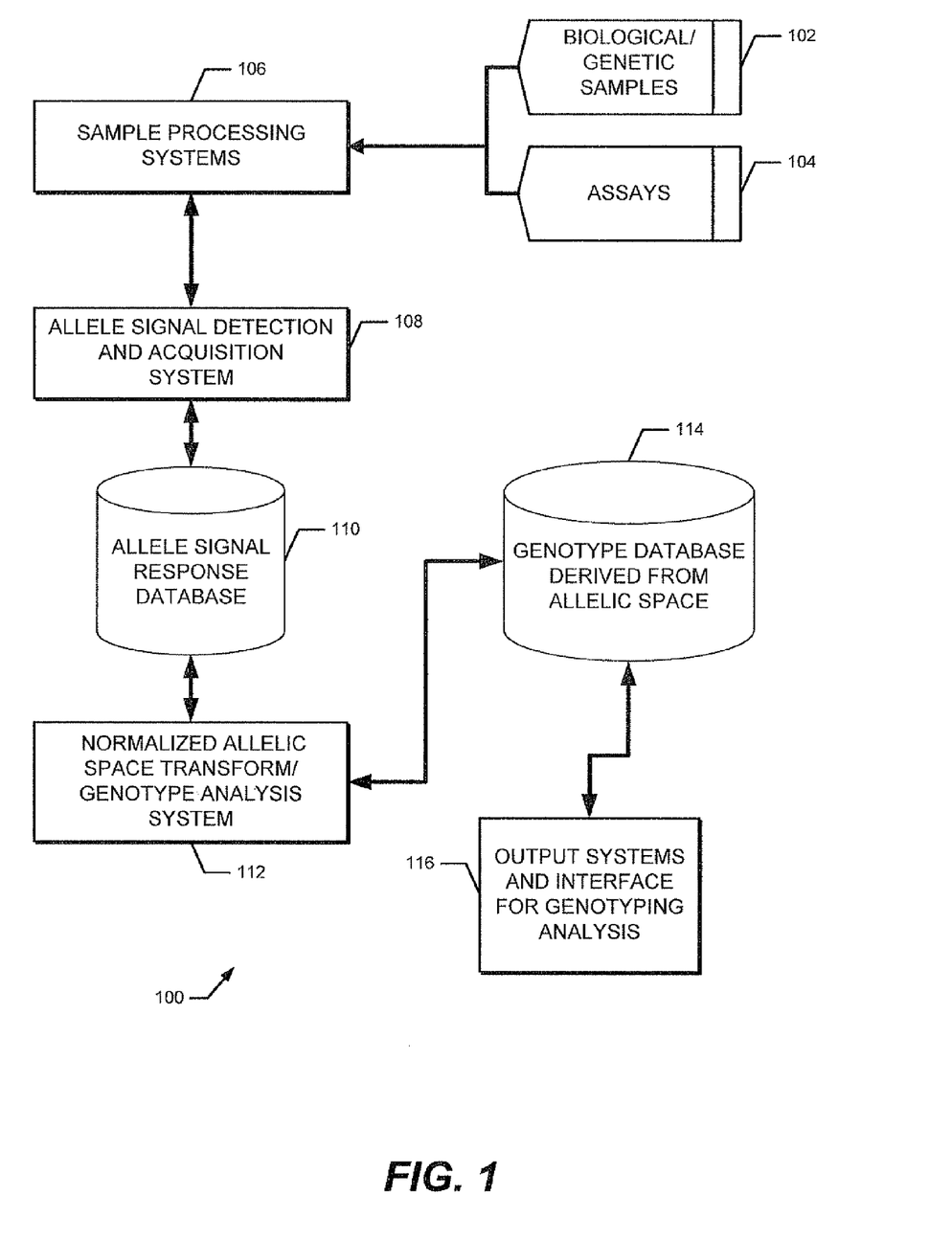
FIG. 1 is a schematic illustration of a system for performing genotyping on genetic samples in accordance with some implementations of the present invention.

FIG. 1 is a schematic illustration of a system configured for genotypic analysis of samples in accordance with some implementations of the present invention. System 100 includes biological/genetic samples 102, assays 104, sample processing systems 106, allele signal detection and acquisition system 108 (hereinafter allelic signal detection system 108), allele signal response database 110, normalized allelic space transform and genotype analysis system 112 (hereinafter normalized allelic space transform system 112), genotype database derived from normalized allelic space 114 and output systems and interface for genotyping analysis 116.

In general, system 100 may be used in genetic and biological research to classify genetic sequence variations in samples 102 that may include insertions, deletions, restriction fragment length polymorphisms ("RFLPSs"), short tandem repeat polymorphisms ("STRPs") and single nucleotide polymorphisms ("SNPs"). Many of the examples and descriptions contained herein below directly relate to this latter SNP type of genetic sequence variation. Detailed analysis SNP is useful in studying the relationship between nucleotide variations and diseases or other conditions. However, SNPs are but one of many different types of nucleotide variations and it is contemplated that application of these concepts with respect to SNPs can also be applied to many other sources of genetic sequence variations described hereinabove and known to those skilled in the art.

Often, a large amount of data may be generated and analyzed when performing a genetic analysis or experiments. For example, this may be accomplished in sample processing systems 106 in part by placing samples in multiple wells and then evaluating with assays 104. In an exemplary application of the present invention, 96 wells of genetic samples may be evaluated with 48 assays 104 sensitive to 48 different SNPs on the genetic samples 102. This results in a total of 4608 different tests to be performed for each tray of samples and a corresponding set of results. Assays 104 can be multiplexed with multiple assays for each sample or singleplexed whereby a single assay can be evaluated individually with each sample.

Allele signal detection system 106 assays the various samples and produces corresponding allele signal response. These signals may be diagrammed using a scatter plot or other diagrammatic representation. In one implementation, allele signal detection system 106 assays utilize a pair of fluorescent probes having an associated discrete marker or reporter dye responsive to each of the different alleles to be detected. During readout of the sample, allele signal detection system 106 records and associates the fluorescent intensities measured for each sample to determine its particular allelic composition. Generally, the results of such an assay are used to determine if a selected sample tested is homozygous for a first allele (e.g., A/A), homozygous for a second allele (e.g., B/B) or heterozygous for a combination of alleles (e.g., A/B).

In one aspect, homozygous portions of the sample tend to exhibit an increased degree of fluorescence in one or another marker type with the amount of observed fluorescence from the opposing marker type significantly diminished or completely absent. Conversely, portions of the sample identified as heterozygous for both alleles (e.g., A/B) typically present a more uniform degree of fluorescence from both markers thus indicating a contribution from two different alleles A and B. A commercial implementation of these operations is performed in Applied Biosystems SNPlex system and Taqman platforms and further employs Applied Biosystems' 3730, 3730x1 and 3100 Prism Genetic Analyzers, Prism 7700 and 7900HT sequence detection systems and Biotrove OpenArray systems to monitor and record the aforementioned amplified fluorescent signals.

In one aspect, the raw data of the resulting allelic signal response is stored in allele signal response database 110. This information may also be represented visually as values in a scatter or cluster plot. Conventional genotyping systems typically represent the allelic signal response data from allele signal response database 110 in such representations to aid in visualization of clusters of signals representing the different genotypes. In some cases, these clusters tend to form three distinct groupings of signal data interpreted as representing a propensity that is homozygous for a first allele (e.g., A/A), homozygous for a second allele (e.g., B/B) or heterozygous for a combination of alleles (e.g., A/B).

In other situations, data may tend to aggregate in greater or fewer than three different clusters. In such instances, it may become difficult to call the allele unambiguously. U.S. patent application Ser. No. 10/611,414 by Holden et al. entitled "A System and Method for SNP Genotype Clustering" (hereinafter Holden) incorporated by reference herein provides at least one approach for clustering analysis and calling genotypes when the distribution of allele signals do not readily and distinctly translate to the different alleles. In Holden, the clusters are discriminated using a relative angular measure of the allele signal response and clusters they form.

Normalized allelic space transform and genotype analysis system 112 (hereinafter normalized allelic space transform system 112) further improves calling an allele by recognizing and compensating for systematic variation that may be present in system 100 and genetic samples 102. For example, this may be introduced from consistent sources of variation inherent to each sample, variation from run to run (i.e., variation in the run), imbalance between the signal response from pairs of complementary alleles (i.e., allelic imbalance) and many other factors that may arise during genotype analysis.

By recognizing and compensating for this variation, the alleles can be called with greater accuracy and in a manner that can be more readily automated for high throughput analytical genotyping systems. In at least one implementation of the present invention, signal response detected from the alleles are transformed from a relative measure of the allelic signal response into a unit-less scalar measure of the various alleles (i.e., homozygous A/B and heterozygous). Through this transformation, the representation of alleles in a normalized allelic space provides a more consistent and more accurate representation of the alleles being measured in a given sample.

Processing performed by normalized allelic space transform 112 also tends to preserve more data and increase the sample sets stored in genotype database derived from normalized allelic space 114. Computer based analytical operations can be performed with fewer exceptions or the need to eliminate data that otherwise would appear as outlying data points or noise. Output systems and interface for genotyping analysis 116 can therefore provide more automated genotyping based on rules rather than requiring visual inspection or subjective viewing of the datasets. For example, a representation of genotypes in the normalized allelic space 114 can be more readily analyzed using a computer and require less visualization and subjective judgment from a user or operator of the analytic equipment used in genotyping.

Figure 2:
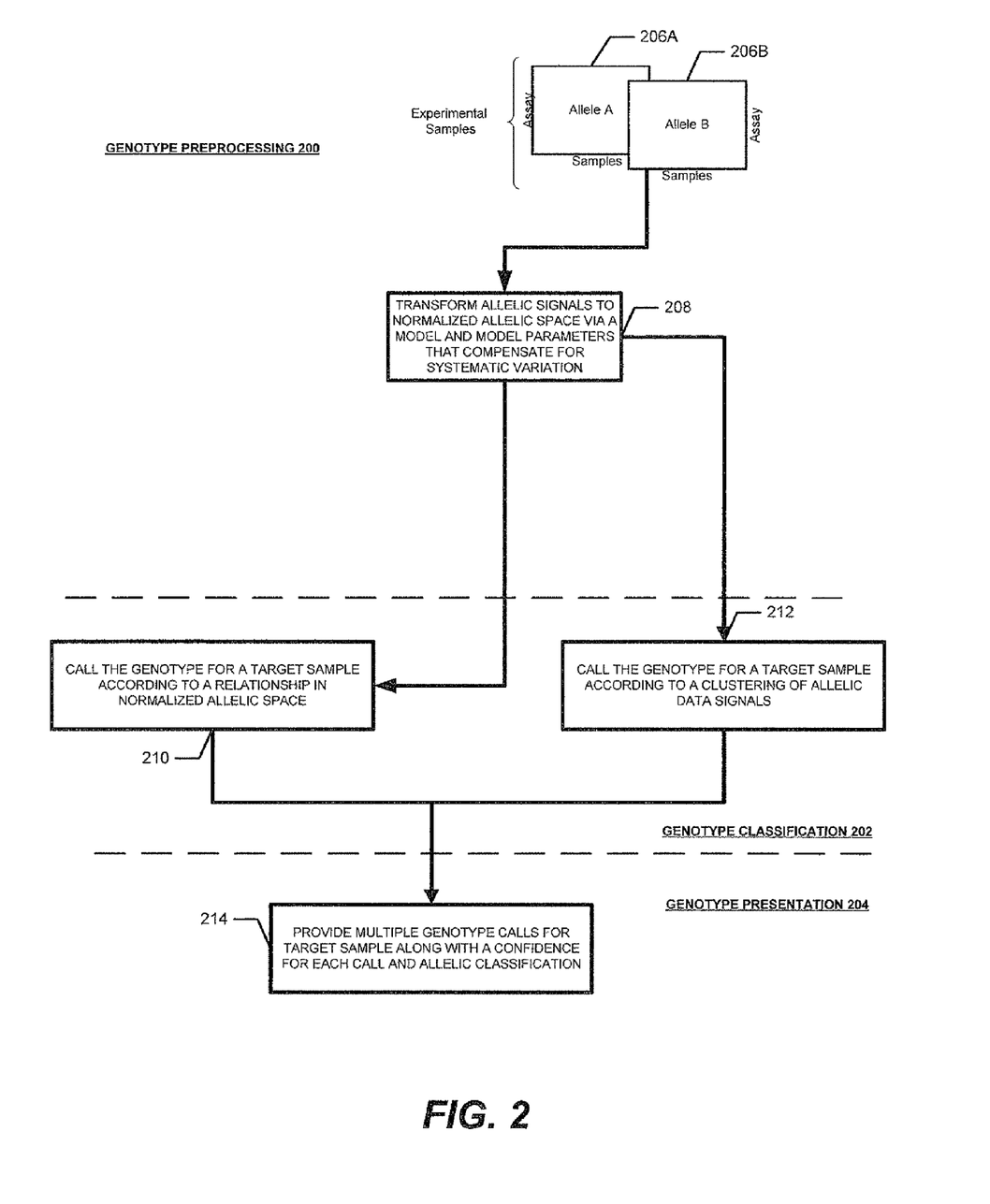
FIG. 2 is a schematic flowchart of the operations used to call genotypes using various aspects of the present invention as well as those available through clustering.

FIG. 2 is a schematic flowchart of the operations used to call genotypes using both aspects of the present invention as well as those available through clustering. The analytical framework for genotyping operations generally works in three stages: a genotype preprocessing 200 a genotype classification 202 and genotype presentation 204 as illustrated in FIG. 2. It is contemplated that the preprocessing transformations of the allelic signals in accordance with aspects of the present invention provides a superior approach to genotype analysis though conventional clustering and other approaches as suggested by Holden should also be considered. Consequently, the operations outlined in FIG. 2 as indicated below include clustering as part of the analytical framework as an option even though genotype calling may be performed with sufficient accuracy without these additional operations or steps in most cases.

In genotype preprocessing 200, allelic signal intensity information is gathered for a combination of experimental samples and corresponding assays as represented by allele A 206 A and allele B 206 B sample matrices. For example, each of 48 assays are applied to 96 samples each tested for two alleles for a total of 9216 measurements contained in both allele A 206 A and allele B 206 B matrices of intensity data points. As previously recognized, these intensity values generally include several sources of systematic variation thus causing the cluster or scatter plots to not exhibit the expected genotype distributions of homozygous A/A, B/B or heterozygous A/B alleles.

In one implementation, it is observed that sources of systematic variation can be attributed to a number of factors including variability in the different samples, variability from one run to another run over time and an imbalance in the signal response from one allele over a complementary allele. As will be described in further detail later herein, implementations of the present invention transform the allelic signals to a normalized allelic space through a model and model parameters that compensate for these identified systematic variations (208). Essentially, this step of the operation not only compensates for these systematic variations but also serves to preserve more data.

Once transformed into the normalized allelic space, implementations of the present invention can then call the genotype for a target sample according to its relationships with expected distributions in normalized allelic space (210). Several approaches can be used to compare the measurements associated with the target experimental sample and the other samples in normalized allelic space. For example, a proximity approach identifies a minimum distance between the target experimental sample and an expected genotype using Cartesian coordinates in the normalized allelic space. An alternative implementation performs additional genotype preprocessing 200 to create a fixed prior probability distribution of alleles normalized in a normalized allelic space. In this operation, training data derived from many different assays, samples and runs are combined together for analysis using a common model and several parameters. It is presumed that each of these data sets are normalized as previously described by identifying an appropriate set of parameters to compensate for the one or more sources of systematic variation. These normalized values are associated with an error function that further refines the distribution presented in the normalized allelic space. Instead of a Cartesian measurement to an expected genotype coordinate, this alternate implementation determines a maximum probability genotype for the target sample as it relates to the error function and neighboring data samples used as training data. Further details on this operation are provided later herein.

In either of the above or other implementations described above or similarly contemplated, genotype classification (212) can also employ conventional clustering as described in Holden. In particular, the call for the genotype of the target sample is performed according to a clustering of the allelic signal response as described in Holden. For example, this may involve measuring a relative angular offset of values for various allelic signals identified for a set of samples and assays. Genotype calls for the target sample in normalized allelic space (210) or based upon clustering of allelic data signals are then presented along with a confidence factor for each call and classification (214).

Figure 3:
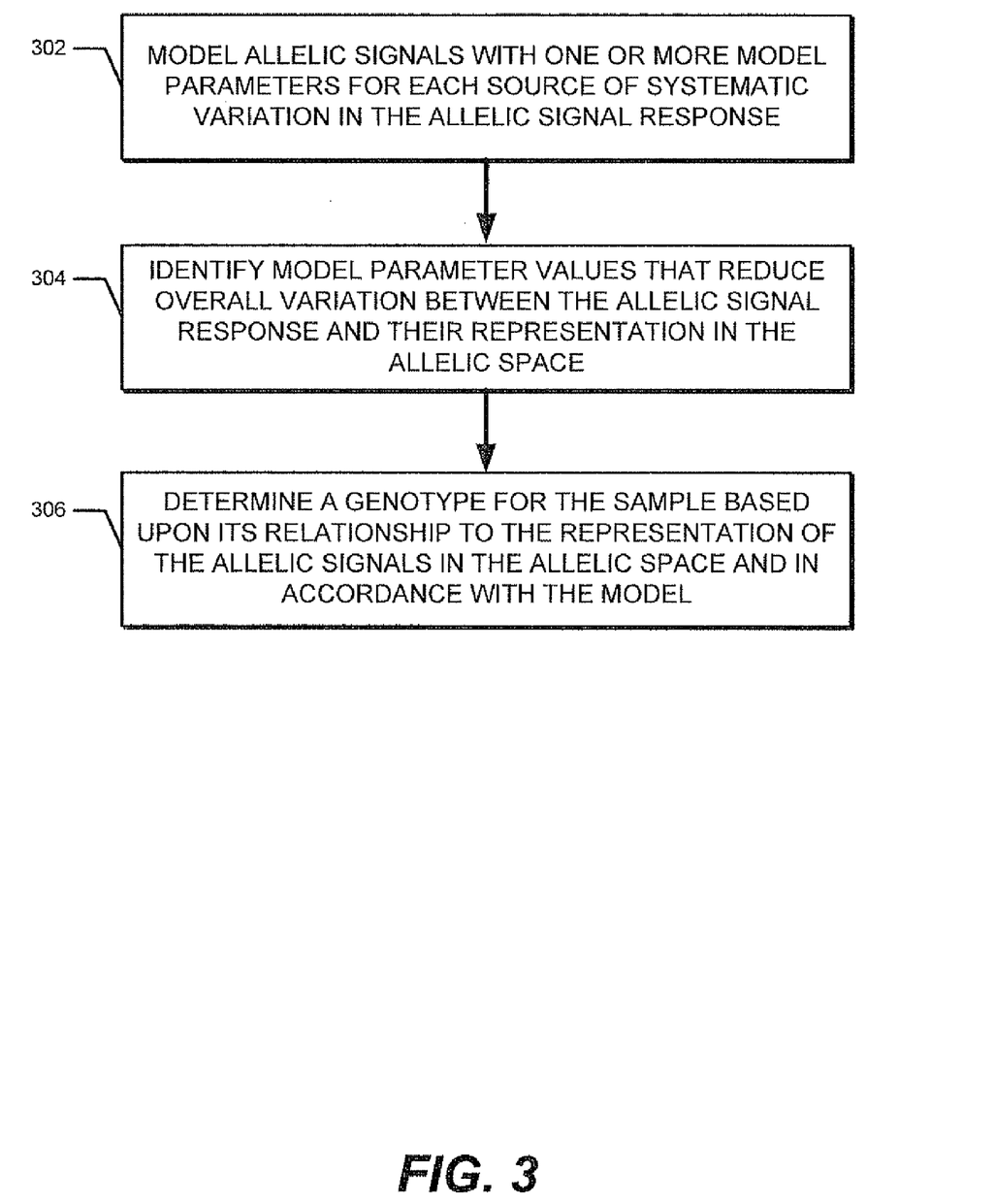
FIG. 3 is a flowchart diagram depicting the operations associated with normalizing the allelic signal response and transforming the signals into an normalized allelic space in accordance with some implementations of the present invention.

Referring now to FIG. 3, a flowchart diagram depicts the operations associated with normalizing the allelic signal response and transforming the signals into a normalized allelic space in accordance with some implementations of the present invention. Implementations of the present invention initially model the allelic signal response with one or more model parameters for each source of systematic variation (302). A basic assumption or constraint for the model is that the normalized signal of any pair of alleles whether homozygous A/A, B/B or heterozygous A/B should sum to unity. Schematically, parameters are incorporated into the model that provide sufficient flexibility to account for a multiplicative variability as contributed by each run, sample and each allele within a SNP assay. Accordingly, one implementation of this model appears below in Equation 1.

$$\gamma \alpha_i \beta_j (A_{ij}/\delta_i + \delta_i B_{ij}) - 1$$

Where:
$A_{ij}$ and $B_{ij}$ are the measured allele signals for SNP assay i and sample j $\gamma$ is a parameter to compensate for variability in the overall run $\alpha_i$ is a parameter to compensate for variability in the SNP assay i $\beta_j$ is a parameter to compensate for variability in the sample j $\delta_i$ is a parameter to compensate for allele imbalance for a SNP assay i and sample j Equation 1

Provided this model in Equation 1 or other useful models, aspects of the present invention identify model parameters that reduce overall variation between the allelic signal response and their representation in the normalized allelic space (304). Essentially, this operation identifies values for the parameters $\alpha$, $\beta$, $\gamma$ and $\delta$ that represent the systematic variation of our measured allelic signal response. One example technique used to identify these parameters minimizes an appropriately selected error function. In Equation 2 provided below, a Chi-square error function is selected to identify the parameters that reduce this overall variation however, it is contemplated that many other error functions could be selected and solved to identify these parameter values.

$$\chi^2 = \sum_{i=1}^{N} \sum_{j=1}^{M} \left[ \frac{\gamma \alpha_i \beta_j (A_{ij}/\delta_i + \delta_i B_{ij}) - 1}{\sigma_{ij}} \right]^2 \quad \text{Equation 2}$$

Where:

$\chi^2$ a Chi-square statistic $\sigma_{ij}$ is an estimation of the error associated with measuring the allelic signal response for a SNP assay $i$ and sample $j$ $N$ is the maximum number of SNP assays $M$ is the maximum number of samples The Chi-square in Equation 2 is a robust statistic often used to process data of uneven quality. Chi-square statistics also behave appropriately as an error function as the values generated are non-negative and its minima usually indicate optimal parameters and describe goodness-of-fit. In this application, the Chi-square statistic operates by comparing the actual, or observed, signal values for each allele compared to the expected signal values if there were no relationship at all between of the set of allele signals in a run made with several samples and SNP assays. The Chi-square statistic in Equation 2 is useful because it tends to discount or reduce weight of data points that may have large error. Likewise, data with smaller error, which should be emphasized, are weighted more heavily.

Minimizing the Chi-square statistic for the allele signals from Equation 2 above can be accomplished by requiring that the first partial derivatives of the Chi-square statistic each be set to zero. This is a requirement to determine an extrema of the Chi-squared statistic. It should be understood that it is typically sufficient to require an extrema of $\chi^2$ as error functions generally do not have maxima. Accordingly, a set of partial first derivatives as found in Equation 3 below can be used to solve for the parameters used in Equation 1 and Equation 2 above without requiring additional constraints on the negativity of second derivatives However, in the case of non-linear equations, some care must be taken to insure that the minimum identified is a global minimum and not merely local minimum.

$$\frac{\partial \chi^2}{\partial \gamma} = 0$$

$$\frac{\partial \chi^2}{\partial \alpha_i} = 0$$

$$\frac{\partial \chi^2}{\partial \delta_i} = 0$$

$$\frac{\partial \chi^2}{\partial \beta_j} = 0$$

Equation 3

Where:

$\frac{\partial \chi^2}{\partial \gamma}$ is partial derivative of Chi-square with respect to $\gamma$, the overall run compensation factor $\frac{\partial \chi^2}{\partial \alpha_i}$ is partial derivative of Chi-square with respect to $\alpha_i$, the SNP assay compensation factor $\frac{\partial \chi^2}{\partial \delta_i}$ is partial derivative of Chi-square with respect to $\delta_i$, the allele balance compensation factor $\frac{\partial \chi^2}{\partial \beta_j}$ is partial derivative of Chi-square with respect to $\beta_j$, the sample compensation factor In some cases, the set of equations in Equation 3 may be degenerate and require additional constraints. In its degenerate form, Equation 3 would not be able to specify the α and β parameters uniquely. For example, it can be seen that the model is insensitive to multiplying the α's by a factor and the β's by its reciprocal. Accordingly, the added constraints to prevent the degenerate condition are described below with respect to Equation 4.

Equation 4

$$\prod_{i=1}^{N} \alpha_i = 1 \quad (1)$$

$$\prod_{j=1}^{M} \beta_j = 1 \quad (2)$$

Where:

$\prod_{i=1}^{N} \alpha_i$ is a repeated product of correction factors for SNP assays having a geometric mean of 1.

$\prod_{j=1}^{M} \beta_j$ is a repeated product of correction factors for the samples having a geometric mean of 1.

To expedite identifying a solution, the non-linear model and constraints provided in Equations 1-4 are recast into separate operations that can be solved quickly with linear algebra. This approach also eliminates concerns of solving these equations and finding local minima rather than the global minima for the function. It also allows the approximate solution to Equation 1 to be found optimally without otherwise expending a computationally significant time to find the solution. It is satisfactory to recast this model into separate steps that can be solved with linear algebra.

First, we temporarily disregard the allele imbalance in Equation 1 by removing $\delta_i$. This provides the following relationship in (1) indicated in Equation 5 below. By substituting the $V_{ij}$ according to the relationship (2) Equation 5, and applying the logarithm to both sides of the equation we have the relationship (3) from Equation 5 below and the linear equation in (4) readily solved in accordance with methods known to those skilled in the art. As a last step subsequent to the solution of (4) and α, β and γ a separate solution can be derived for an allele-balancing factor, δ.

$$\gamma \alpha_i \beta_j (A_{ij} + B_{ij}) = 1 \quad (1)$$

$$V_{ij} = A_{ij} + B_{ij} \quad (2)$$

$$\log(\gamma \alpha_i \beta_j V_{ij}) = 0 \quad (3)$$

$$g + a_i + b_j + u_{ij} = 0 \quad (4)$$

Where:
g=log γ
$a_i$=log $\alpha_i$
$b_j$=log $\beta_j$
$u_{ij}$=log $V_{ij}$

Equation 5

Once determined, the parameters are then applied to the measured allele signals to transform our allele pairs into a normalized allelic space rather than the allelic signal space originally measured. This resulting normalized allelic space may be universally used as it is largely free of systematic instrument and chemistry artifacts and can be used across runs as well as samples, and alleles within a SNP assays. The conversion between the signal response between alleles $A_{ij}$ and $B_{ij}$ and the corresponding values in normalized allelic space of $a_{ij}$ and $b_{ij}$ is defined by the relationships in Equation 6.

$$a_{ij} = \gamma \alpha_i \beta_j A_{ij} / \delta_i$$

$$b_{ij} = \gamma \alpha_i \beta_j \delta_i B_{ij}$$

Where:

$a_{ij}$ is a allele signal response mapped into the allelic space for allele $A_{ij}$ $b_{ij}$ is a allele signal response mapped into the allelic space for allele $B_{ij}$ Equation 6

Systematic variation in raw allele signal $A_{ij}$ and $B_{ij}$ is compensated through Equation 6 generating normalized allele signals $a_{ij}$ and $b_{ij}$ in the normalized allelic space. The genotyping is then determined for the sample based upon the relationship to the representation of the allelic signals in this normalized allelic space and in accordance with the model (306). Details on this determination is provided in further detail later herein.

Figure 4A:
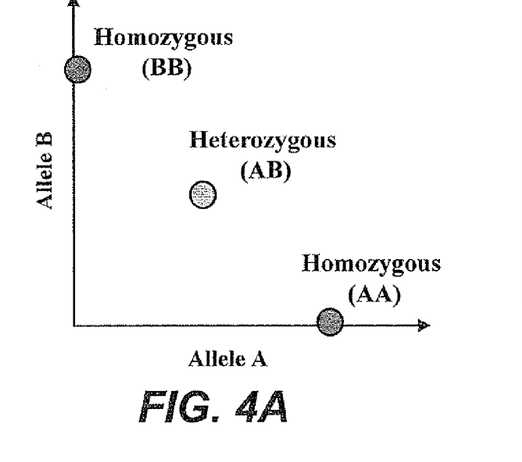
FIG. 4A is a schematic representation that illustrates the expected genotype values and basis for some of the constraints used by some implementations of the present invention.

In FIG. 4A, a schematic representation illustrates the expected genotype values and basis for some of the constraints used by some implementations of the present invention. In particular, three different possible alleles are mapped in a unit space at expected genotype values along Cartesian coordinates (1, 0), (½, ½) and (0, 1). Each of the genotype value coordinates corresponds to homozygous AA alleles, heterozygous AB alleles and homozygous BB alleles with an expectation that sum of each genotype pair is unity or one.

Figure 4B:
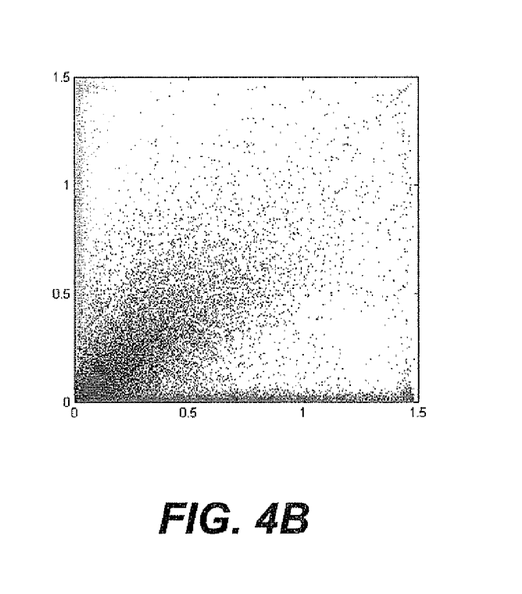
FIG. 4B illustrates the more random appearing distribution of allelic signals before normalization and processing performed in accordance with some aspects of the present invention.

As a point of comparison, FIG. 4B illustrates the more random appearing distribution of approximately eighty-thousand pairs of allelic signals before normalization and processing performed in accordance with some aspects of the present invention. Namely, the scatter plot of allele signal intensity points in FIG. 4B do not appear to form three distinct representation of the expected genotypes from FIG. 4A but instead provide ambiguous information about the relative existence of one allele over another.

Figure 4C:
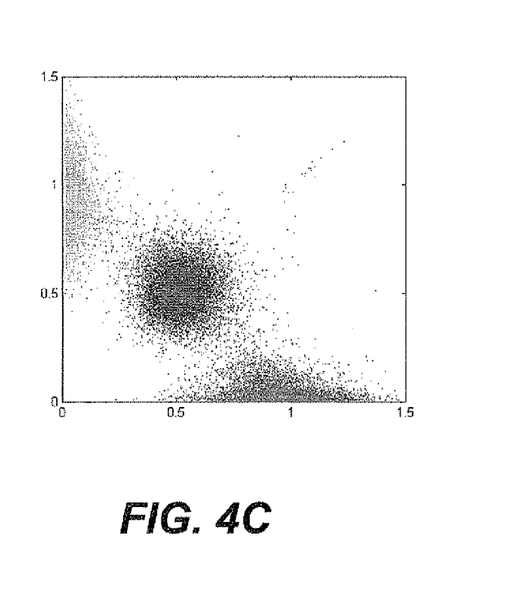
FIG. 4C illustrates the effect of normalization on allelic signal data from FIG. 4B.

In contrast, FIG. 4C illustrates a rather distinct grouping of the three expected genotypes in a unit space as illustrated in FIG. 4A. The points in FIG. 4C fall into the expected genotype values as set forth in FIG. 4A and encompassed by the model and parameters used to normalize the values from FIG. 4B as provided in Equation 1 through Equation 6 provided hereinabove. Normalization not only removes ambiguity of the values presented in the conventional scatter plot but also serves to preserve data otherwise considered outlying and noisy by normal clustering and other analytical genotyping tools.

Figure 4D:
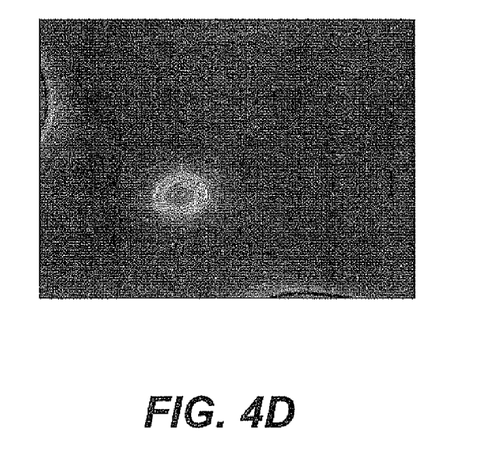
FIG. 4D illustrates the distribution of a large number of normalized training genotypes used to develop the prior probability distributions for the three expected genotypes.

FIG. 4D provides yet another distinct grouping of the three expected genotypes in accordance with other aspects of the present invention. These contours are frequency determinations of a training set that are subsequently used to fit prior probability distributions. In particular, the genotypes and parameters fitted to an elliptical Gaussian distribution provide even more differentiation between the alleles.

Figure 5A:
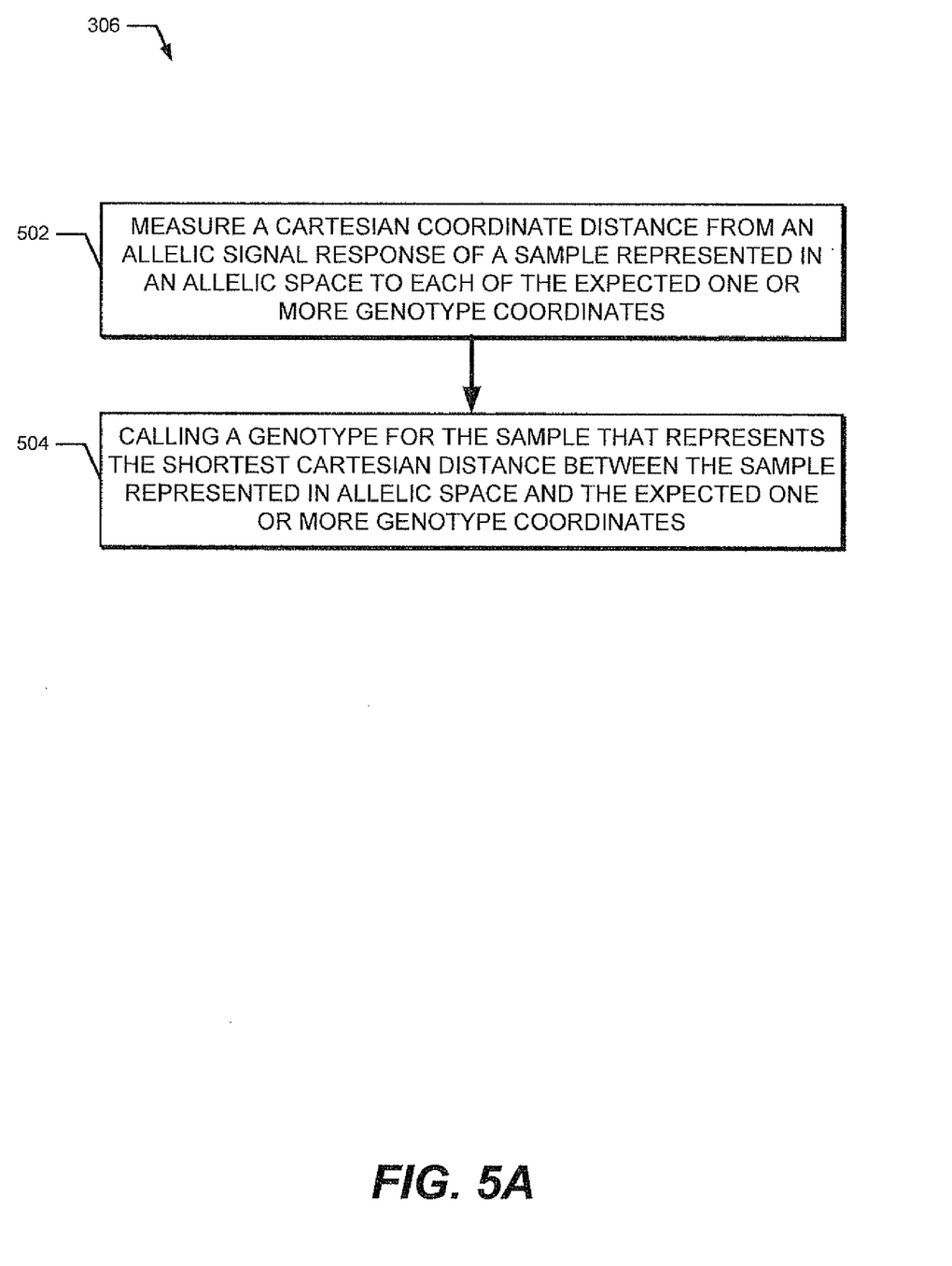
FIG. 5A presents the operations of using a Cartesian coordinate system in the normalized allelic space to call the genotype for a given sample.

In light of the distribution illustrated in FIG. 4C, calling a genotype can readily be determined immediately and without the need for clustering. FIG. 5A presents the operations of using a Cartesian coordinate system in the normalized allelic space to call the genotype for a given sample. This is sometimes referred to as a proximity genotyping approach. Using the normalized allelic space representation, implementations of the present invention measure a Cartesian coordinate distance from an allelic signal response represented in the normalized allelic space to each of the expected one or more genotype coordinates (502). For example, the expected genotype coordinates for homozygous alleles AA, heterozygous alleles AB and homozygous alleles BB corresponds to coordinates (1,0), (½, ½) and (0,1) for the unit based normalized allelic space.

Next, various implementations of the present invention call a genotype for the sample that represents the shortest Cartesian distance between the sample represented in normalized allelic space and the expected one or more genotype coordinates for each allele (504). As previously described, clustering can also be used as an additional indicia for genotyping but may not be required given the relatively straightforward ability to call the genotype in the normalized allelic space.

Figure 5B:
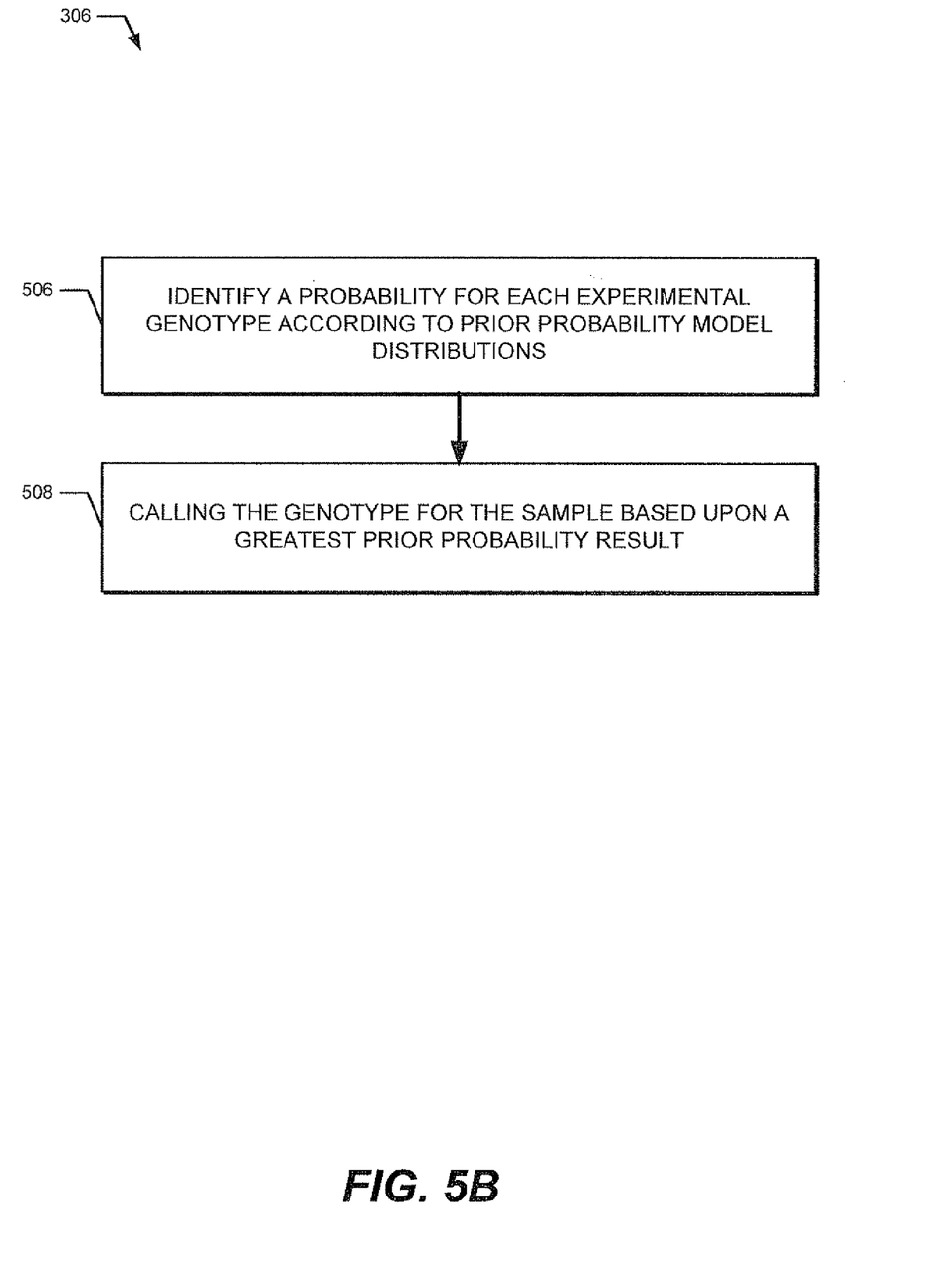
FIG. 5B provides an alternative approach to calling genotypes using a fixed prior probability distribution in accordance with implementations of the present

Likewise, the prior probability distribution illustrated in FIG. 4D also facilitates calling a genotype immediately and without the need for clustering. FIG. 5B provides an alternative approach to calling genotypes using a fixed prior probability distribution in accordance with implementations of the present invention. Initially, this approach identifies a probability of each experimental genotype according to the prior probability model distributions (506). Normalized allelic values for each experimental genotype are used in the equations that describe the prior probability distribution. For example, the normalized allelic values are entered into a set of elliptical Gaussian equations. Details on determining the fixed prior probability distribution are described herein below in FIG. 5C. Next, the genotype for the experimental sample is called based upon the greatest prior probability result (506). In practice, calling the genotype for the experimental sample is based upon a greatest prior probability and reflected by the probability distribution as applied to the sample normalized in normalized allelic space. The highest resulting probability indicates the most likely genotype for the experimental sample.

Figure 5C:
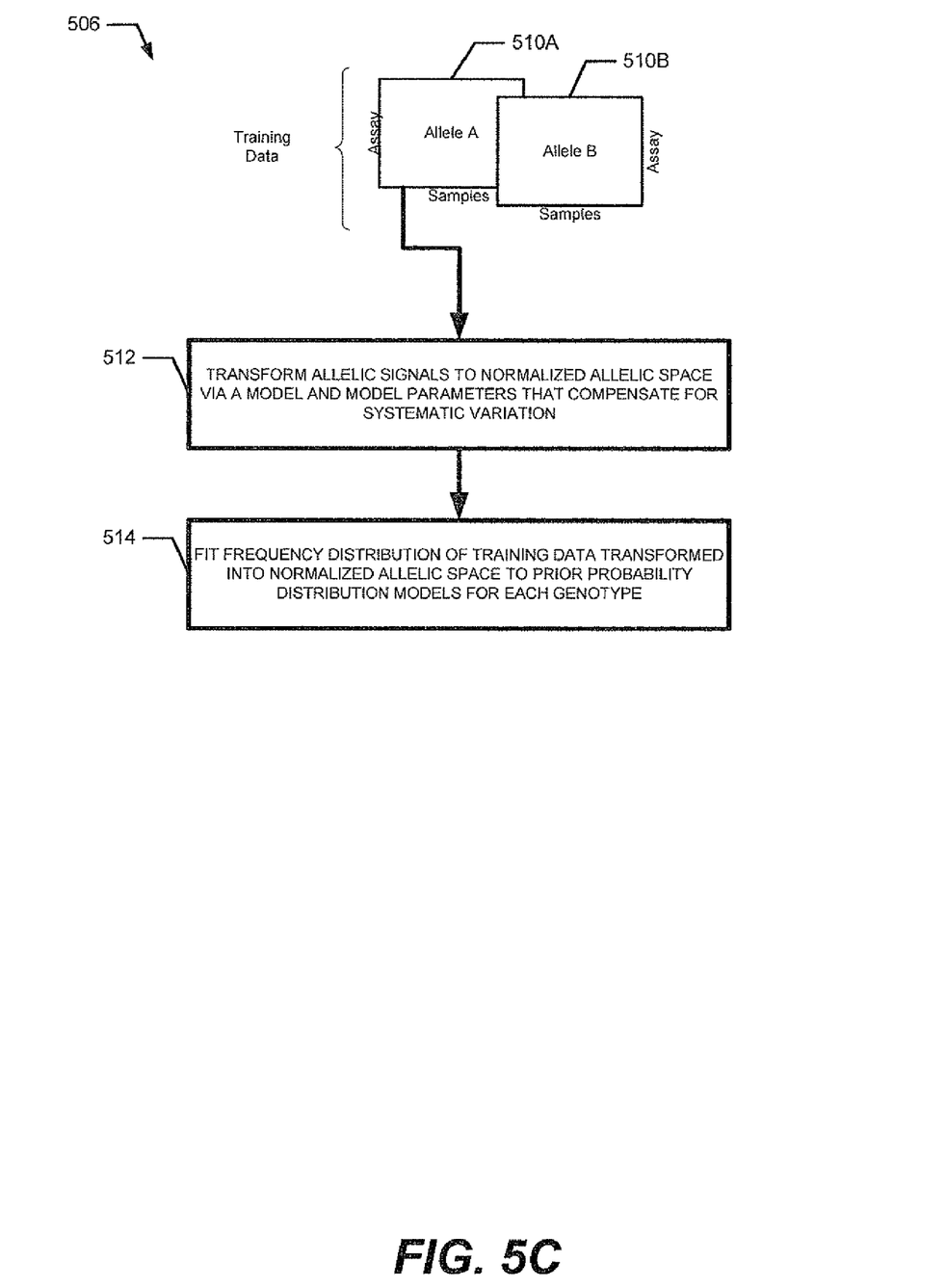
FIG. 5C is a flowchart diagram of the operations for generating the fixed prior probability distribution used in calling the genotypes

FIG. 5C is a flowchart diagram of the operations for generating the fixed prior probability distribution used in calling the genotypes. Initially, a large set of training data genotypes 510A and 510B are used to establish the prior probability distribution. Essentially, the frequency of occurrence of these normalized signals in the training set is what establishes the expected distribution in normalized allelic space subsequent genotype samples. As before, the systematic variation is compensated for by normalizing and transforming the allelic signal response of the various training genotypes into scalar values in normalized allelic space (512). Various implementations of the present invention fit the normalized set of genotype training data to one or more probability distributions that reflects the set of alleles (610). In some implementations, the distribution can be modeled using three elliptical Gaussian distributions as described by the general form set formed in Equation 7 below.

$$F(a,b) = F e^{-(a-a_o)^2/s_a^2 - (b-b_o)^2/s_b^2}$$

Where:

a is a normalized allele A in the allelic space b is a normalized allele B in the allelic space $F_o$ is a model parameter $S_b^2$ is a measure of the dimension of the ellipse along the axis of allele b in allelic space $S_a^2$ is a measure of the dimension of the ellipse along the axis of allele a in allelic space $a_o$ is an offset for the center of the ellipse along the axis of allele a in allelic space $b_o$ is an offset for the center of the ellipse along the axis of allele b in allelic space Equation 7

Equation 8 provides a more specific set of equations for the prior probability distributions provided that $a_o$ and $b_o$ are the expected genotype coordinates (a,b) for homozygous allele AA, heterozygous allele AB and homozygous allele BB with corresponding coordinates (1,0), (½, ½) and (0,1) in the unit based normalized allelic space.

$$\text{Homozygous}_{aa}(a,b) = Fe^{-(a-1)^2/s_a^2 - (b-0)^2/s_b^2}$$

$$\text{Heterozygous}_{ab}(a,b) = Fe^{-(a-1/2)^2/s_a^2 - (b-1/2)^2/s_b^2}$$

$$\text{Homozygous}_{bb}(a,b) = Fe^{-(a-0)^2/s_a^2 - (b-1)^2/s_b^2}$$

Equation 8

Figure 6:
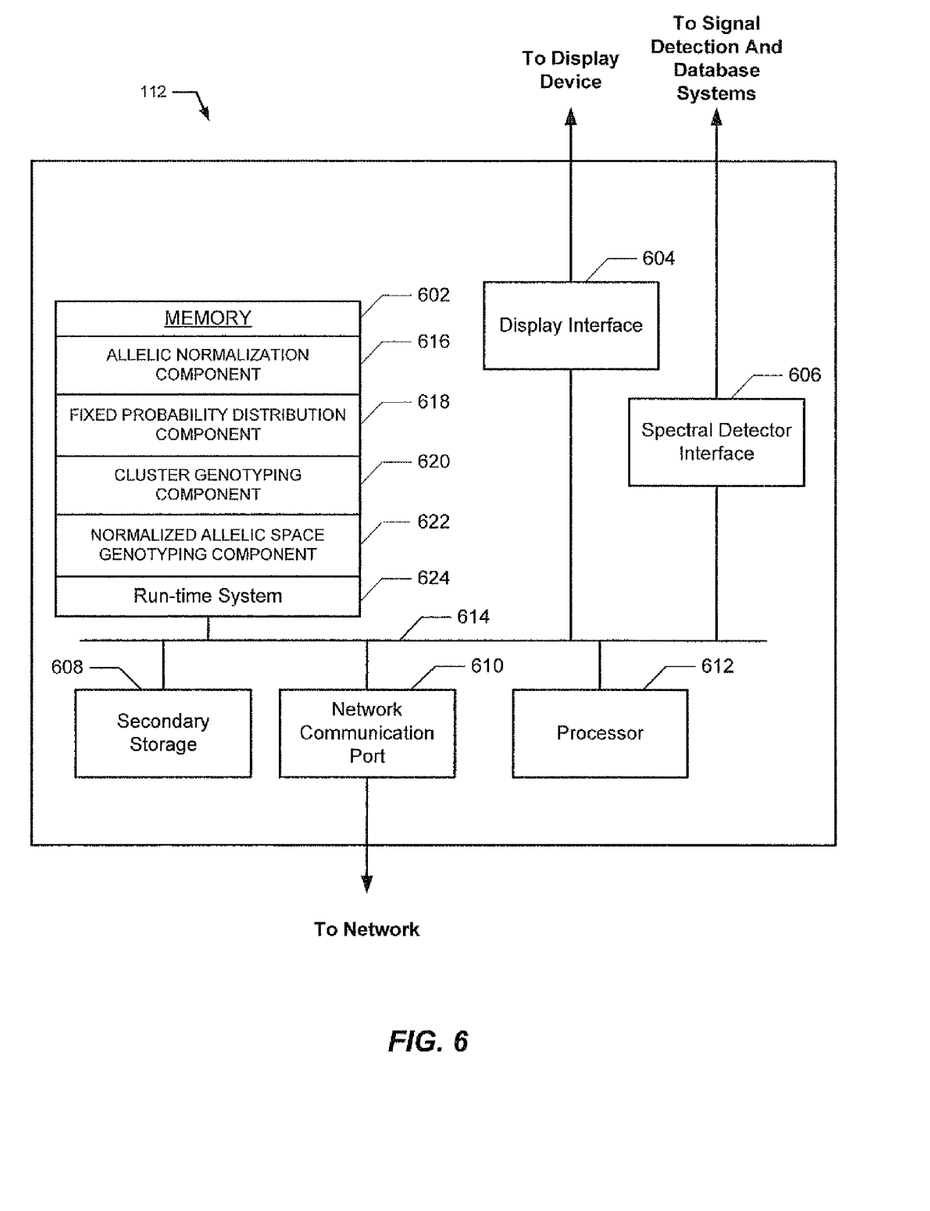
FIG. 6 depicts a schematic system and methods for calling genotypes in accordance with implementations of the present invention.

FIG. 6 depicts a schematic system 112 and methods for calling genotypes in accordance with implementations of the present invention. System 112 includes a memory 602 to hold executing programs typically random access memory (RAM) or read-only memory (ROM) such as Flash, a display interface 604, a spectral detector interface 606, a secondary storage 608, a network communication port 610, and a processor 612, operatively coupled together over an interconnect 614.

Display interface 604 allows presentation of information related to genotyping in normalized allelic space and with clustering of signals. Spectral detector interface 606 contains circuitry to control operation of a spectral detector including duplex transmission of data in real-time or in a batch operation. Secondary storage 608 can contain experimental results and programs for long-term storage including allelic signal response data, normalized allelic space transformation data, normalized and raw genotype training data, target samples and other data useful in genotyping in accordance with aspects of the present invention. Network communication port 601 transmits and receives results and data over a network to other computer systems and databases. Processor 612 executes the routines and modules contained in memory 602.

In the illustration, memory 602 includes allelic normalization component 616, fixed prior probability distribution component 618, cluster genotyping component 620, normalized allelic space genotyping component 622 and a run-time system 628 for managing computing resources used in conjunction with one or more of the above components.

Allelic normalization component 616 contains routines to transform allelic signals in a signal domain to scalar values in the normalized allelic space described previously. Essentially, this component uses a model and corresponding model parameters to compensate for systematic variation in the one or more allelic signals detected.

Fixed prior probability distribution component 618 gathers many data points from various runs, samples and SNP assays to create a probability distribution and basis for genotyping new samples. As previously described, the prior probability distribution in normalized allelic space can be further modeled using a Gaussian elliptical representation for each of the homozygous alleles (both AA and BB) as well as the heterozygous allele.

Run-time system 628 manages system resources used when processing one or more of the previously mentioned modules. For example, run-time system 628 can be a general-purpose operating system, an embedded operating system or a real-time operating system or controller.

System 112 can be preprogrammed, in ROM, for example, using field-programmable gate array (FPGA) technology or it can be programmed (and reprogrammed) by loading a program from another source (for example, from a floppy disk, an ordinary disk drive, a CD-ROM, or another computer). In addition, system 112 can be implemented using customized application specific integrated circuits (ASICs).

Having thus described various implementations and embodiments of the present invention, it should be noted by those skilled in the art that the disclosures are exemplary only and that various other alternatives, adaptations and modifications may be made within the scope of the present invention. For example, it is mentioned that aspects of the present invention are useful for genotyping as it relates to SNPs and SNP assays. However, it is also contemplated that the teachings performed in accordance with implementations of the present invention can also be performed to facilitate genotyping of insertions, deletions, restriction fragment length polymorphisms ("RFLPSs"), short tandem repeat polymorphisms ("STRPs") as well as single nucleotide polymorphisms ("SNPs").

Embodiments of the invention can be implemented in digital electronic circuitry, or in computer hardware, firmware, software, or in combinations of thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs.

Thus, the invention is not limited to the specific embodiments described and illustrated above. Instead, the invention is construed according to the claims that follow and the full-scope of their equivalents thereof.

The invention claimed is:

1. A computer implemented method of generating genotype calls for a sample comprising:
    modeling, by a processor, allelic signal response into an allelic model having one or more model parameters for an identified one or more sources of systematic variation;
    transforming, by the processor, the allelic signals through the one or more model parameters of the allelic model to a normalized allelic space that serves to compensate for the one or more sources of systematic variation;
    determining, by the processor, a genotype for the sample based upon its relationship to the representation of the allelic signals in normalized allelic space and in accordance with the allelic model;
    creating, by the processor, a fixed prior probability distribution of normalized allele signals from a statistically significant training set of genotype data by fitting a normalized training set of genotype data to probability distributions that reflect a set of allowed genotypes in the normalized allelic space, wherein the probability distributions are based upon elliptical Gaussian probability distributions; and calling, by the processor, the genotype for the sample based upon a greatest prior probability as reflected by the fitted probability distribution and applied to the sample normalized in the normalized allelic space.

2. The computer implemented method of claim 1 wherein determining the genotype for the sample further comprises, measuring a Cartesian distance from a sample represented in the normalized allelic space to an expected one or more genotype coordinates; and calling a genotype for the sample that represents the shortest measured Cartesian distance between the sample and one of the expected one or more genotype coordinates.

3. The method of claim 2 wherein the expected one or more genotype coordinates is selected from a set of genotype coordinates including: a homozygous allele A, a heterozygous allele AB and a homozygous allele B having corresponding coordinates (1, 0), (½, ½) and (0, 1) respectively.

4. The computer implemented method of claim 1 wherein the elliptical Gaussian probability distribution for the set of alleles normalized in the normalized allelic space is represented by the following equations:

$$\text{Homozygous}_{aa}(a,b) = Fe^{-(a-1)^2/s_a^2 - (b-0)^2/s_b^2}$$

$$\text{Heterozygous}_{ab}(a,b) = Fe^{-(a-1/2)^2/s_a^2 - (b-1/2)^2/s_b^2}$$

$$\text{Homozygous}_{bb}(a,b) = Fe^{-(a-0)^2/s_a^2 - (b-1)^2/s_b^2}$$

where:
a is a normalized allele A in the allelic space;
b is a normalized allele B in the allelic space;
$s_b^2$ is a measure of the dimension of the ellipse along the axis of allele b in allelic space; and
$s_a^2$ is a measure of the dimension of the ellipse along the axis of allele a in allelic space.

5. The computer implemented method of claim 1 wherein the systematic variation in allelic signals is selected from a set of systematic factors including: a sample variability, an experimental run variability and an allelic imbalance.

6. The computer implemented method of claim 1 wherein the parameter associated with each source of systematic variation is modified to minimize overall variation in the allelic signals and a model of the alleles in a training population.

7. The computer implemented method of claim 1 wherein the model of the alleles in the training population are assigned a unit probability of occurrence in the allele space of homozygous and heterozygous alleles.

8. The computer implemented method of claim 6 wherein the model of the alleles $A_{ij}$ and $B_{ij}$ in the training population are fit to a linear function as follows:

$$\gamma \alpha_i \beta_j (A_{ij}/\delta_i + \delta_i B_{ij}) = 1$$

Where:
$A_{ij}$ and $B_{ij}$ are the measured allele signals for SNP assay i and sample j
$\gamma$ is a parameter to compensate for variability in the overall run
$\alpha_i$ is a parameter to compensate for variability in the SNP assay i
$\beta_j$ is a parameter to compensate for variability in the sample j $\delta_i$ is a parameter to compensate for allele imbalance for a SNP assay i and sample j.

9. A non-transitory computer program product for generating genotype calls for a sample, comprising instructions operable to cause a programmable processor to:

model allelic signal response into an allelic model having one or more model parameters for an identified one or more sources of systematic variation;

transform the allelic signals through the one or more model parameters of the allelic model to a normalized allelic space that serves to compensate for the one or more sources of systematic variation;

determine a genotype for the sample based upon its relationship to the representation of the allelic signals in normalized allelic space and in accordance with the allelic model;

create fixed prior probability distribution of normalized allele signals from a statistically significant training set of genotype data by fitting a normalized training set of genotype data to probability distributions that reflect a set of allowed genotypes in the normalized allelic space, wherein the probability distributions are based upon elliptical Gaussian probability distributions; and call the genotype for the sample based upon a greatest prior probability as reflected by the fitted probability distribution and applied to the sample normalized in the normalized allelic space.

10. The non-transitory computer program product of claim 9 wherein the expected one or more genotype coordinates is selected from a set of genotype coordinates including: a homozygous allele A, a heterozygous allele AB and a homozygous allele B having corresponding coordinates (1, 0), (½, ½) and (0, 1) respectively.

11. The non-transitory computer program product of claim 9 wherein the elliptical Gaussian probability distribution for the set of alleles normalized in the normalized allelic space is represented by the following equations:

$$\text{Homozygous}_{aa}(a,b) = Fe^{-(a-1)^2/s_a^2 - (b-0)^2/s_b^2}$$

$$\text{Heterozygous}_{ab}(a,b) = Fe^{-(a-1/2)^2/s_a^2 - (b-1/2)^2/s_b^2}$$

$$\text{Homozygous}_{bb}(a,b) = Fe^{-(a-0)^2/s_a^2 - (b-1)^2/s_b^2}$$

where:
a is a normalized allele A in the allelic space;
b is a normalized allele B in the allelic space;
$s_b^2$ is a measure of the dimension of the ellipse along the axis of allele b in allelic space; and
$s_a^2$ is a measure of the dimension of the ellipse along the axis of allele a in allelic space.

12. An apparatus for generating genotype calls for a sample, comprising:
a processor; and
a memory storing instructions, executable by the processor, for:
modeling allelic signal response into an allelic model having one or more model parameters for an identified one or more sources of systematic variation;
transforming the allelic signals through the one or more model parameters of the allelic model to a normalized allelic space that serves to compensate for the one or more sources of systematic variation;
determining a genotype for the sample based upon its relationship to the representation of the allelic signals in normalized allelic space and in accordance with the allelic model;

creating a fixed prior probability distribution of normalized allele signals from a statistically significant training set of genotype data by fitting a normalized training set of genotype data to probability distributions that reflect a set of allowed genotypes in the normalized allelic space, wherein the probability distributions are based upon elliptical Gaussian probability distributions; and calling the genotype for the sample based upon a greatest prior probability as reflected by the fitted probability distribution and applied to the sample normalized in the normalized allelic space.

13. The apparatus of claim 12 wherein the expected one or more genotype coordinates is selected from a set of genotype coordinates including: a homozygous allele A, a heterozygous allele AB and a homozygous allele B having corresponding coordinates (1, 0), (½, ½) and (0, 1) respectively.

14. The apparatus of claim 12 wherein determining the genotype for the sample further comprises,
 presenting the cluster of allelic data signals in a diagram along with a confidence factor for the sample and genotype classification.

* * * * *